United States Patent
Triva

(10) Patent No.: US 11,446,012 B2
(45) Date of Patent: *Sep. 20, 2022

(54) SWAB FOR COLLECTING BIOLOGICAL SPECIMENS

(71) Applicant: Copan Italia S.p.A., Brescia (IT)

(72) Inventor: Daniele Triva, Brescia (IT)

(73) Assignee: Copan Italia S.p.A., Brescia (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/744,421

(22) Filed: May 13, 2022

(65) Prior Publication Data

US 2022/0265251 A1    Aug. 25, 2022

Related U.S. Application Data

(63) Continuation of application No. 13/657,949, filed on Oct. 23, 2012, now Pat. No. 11,364,018, which is a continuation of application No. 12/903,921, filed on Oct. 13, 2010, now Pat. No. 8,317,728, which is a continuation of application No. 10/543,873, filed as application No. PCT/EP2004/003392 on Mar. 31, 2004, now Pat. No. 8,114,027.

(30) Foreign Application Priority Data

Apr. 1, 2003 (IT) .............................. MI2003A0643

(51) Int. Cl.
| | |
|---|---|
| A61B 10/00 | (2006.01) |
| A61F 13/38 | (2006.01) |
| B01L 3/00 | (2006.01) |
| C12M 1/30 | (2006.01) |

(52) U.S. Cl.
CPC .......... *A61B 10/0045* (2013.01); *A61F 13/38* (2013.01); *B01L 3/5029* (2013.01); *C12M 33/02* (2013.01); *B01L 2200/087* (2013.01); *B01L 2300/0832* (2013.01); *B01L 2300/161* (2013.01)

(58) Field of Classification Search
CPC .... A61F 13/38; C12M 33/02; A61B 10/0045; B01L 3/5029; B01L 2200/087; B01L 2300/161; B01L 2300/0832
See application file for complete search history.

(56) References Cited

U.S. PATENT DOCUMENTS

| | | | |
|---|---|---|---|
| 3,163,160 A | 12/1964 | Cohen | |
| 3,434,801 A | 3/1969 | Scherr | |
| 3,744,499 A | 7/1973 | Wells | |
| 3,776,753 A | 12/1973 | Habib | |

(Continued)

FOREIGN PATENT DOCUMENTS

| | | |
|---|---|---|
| CN | 1070850 | 4/1993 |
| CN | 2183735 | 11/1994 |

(Continued)

OTHER PUBLICATIONS

"Flock 2003" Int. Flock Symposium, Apr. 2003, Dresden, 3 pages.

(Continued)

*Primary Examiner* — David J. McCrosky
(74) *Attorney, Agent, or Firm* — Fish & Richardson P.C.

(57) ABSTRACT

A method for collecting biological specimens using a swab of the type consisting of a rod terminating in a tip covered with fiber with hydrophilic properties to allow absorption of said specimens, wherein said fiber covers said tip in the form of a layer deposited by flocking.

30 Claims, 1 Drawing Sheet

(56) References Cited

U.S. PATENT DOCUMENTS

| | | |
|---|---|---|
| 3,792,699 A | 2/1974 | Tobin et al. |
| 3,854,319 A | 12/1974 | Burroughs et al. |
| 3,881,464 A | 5/1975 | Levene |
| 3,888,629 A | 6/1975 | Bagshawe |
| 3,900,651 A | 8/1975 | Hoppe et al. |
| 3,954,563 A | 5/1976 | Mennen |
| 4,030,978 A | 6/1977 | Abramson |
| 4,039,934 A | 8/1977 | Ostashko et al. |
| 4,175,560 A | 11/1979 | Knoll |
| 4,196,167 A | 4/1980 | Olsen |
| 4,227,537 A | 10/1980 | Suciu et al. |
| 4,234,316 A | 11/1980 | Hevey |
| 4,307,152 A | 12/1981 | Mathes et al. |
| 4,326,545 A | 4/1982 | Motegi et al. |
| 4,340,670 A | 7/1982 | Mennen |
| 4,371,485 A | 2/1983 | Mathes et al. |
| 4,421,809 A | 12/1983 | Bish et al. |
| 4,454,109 A | 6/1984 | Hillman |
| 4,525,452 A | 6/1985 | Jones |
| 4,612,147 A | 9/1986 | Haubold et al. |
| 4,687,257 A | 8/1987 | Stem |
| 4,707,450 A | 11/1987 | Nason |
| 4,719,181 A | 1/1988 | Schobel et al. |
| 4,734,964 A | 4/1988 | Lane et al. |
| 4,749,655 A | 6/1988 | Monthony et al. |
| 4,754,764 A | 7/1988 | Bayne |
| 4,759,376 A | 7/1988 | Stormby |
| 4,767,398 A | 8/1988 | Blasius, Jr. |
| 4,789,639 A | 12/1988 | Fleming |
| 4,796,647 A | 1/1989 | Gueret |
| 4,856,136 A | 8/1989 | Janssen |
| 4,861,343 A | 8/1989 | Neunzig |
| 4,873,992 A | 10/1989 | Bayne |
| 4,877,036 A | 10/1989 | Saint-Amand |
| 4,877,037 A | 10/1989 | Ko et al. |
| 4,922,936 A | 5/1990 | Buzzi et al. |
| 4,953,560 A | 9/1990 | Samuels |
| 4,974,980 A | 12/1990 | Gueret |
| 5,009,846 A | 4/1991 | Gavet et al. |
| 5,022,408 A | 6/1991 | Mohajer |
| 5,091,153 A | 2/1992 | Bachand |
| 5,163,441 A | 11/1992 | Monthony et al. |
| 5,279,964 A | 1/1994 | Chrisope |
| 5,324,128 A | 6/1994 | Gueret |
| 5,370,992 A | 12/1994 | Shah |
| 5,418,136 A | 5/1995 | Miller |
| 5,460,781 A | 10/1995 | Hori |
| 5,468,606 A | 11/1995 | Bogart |
| 5,538,732 A | 7/1996 | Smith et al. |
| 5,614,375 A | 3/1997 | Citri |
| 5,623,941 A | 4/1997 | Hedberg et al. |
| 5,627,071 A | 5/1997 | Triva |
| 5,676,643 A | 10/1997 | Cann et al. |
| 5,704,388 A | 1/1998 | Freeman |
| 5,710,041 A | 1/1998 | Moorman et al. |
| 5,738,643 A | 4/1998 | Stredic, III |
| 5,846,215 A | 12/1998 | Zygmont |
| 5,869,003 A | 2/1999 | Nason |
| 5,899,622 A | 5/1999 | Gueret |
| 5,928,176 A | 7/1999 | Nakatani |
| 5,944,519 A | 8/1999 | Griffiths |
| 6,010,462 A | 1/2000 | Stoermer, III |
| 6,033,143 A | 3/2000 | Gueret |
| 6,080,126 A | 6/2000 | Zygmont |
| 6,049,934 A | 8/2000 | Discko |
| 6,232,567 B1 | 5/2001 | Bonino et al. |
| 6,286,246 B1 | 9/2001 | Rachal et al. |
| 6,306,498 B1 | 10/2001 | Yuuki et al. |
| 6,328,159 B1 | 12/2001 | Discko |
| 6,341,912 B1 | 1/2002 | Gueret |
| 6,352,513 B1 | 3/2002 | Anderson et al. |
| 6,365,794 B1 | 4/2002 | Dabi et al. |
| 6,376,025 B1 | 4/2002 | Mark |
| 6,382,972 B1 | 5/2002 | Fischer et al. |
| 6,413,087 B1 | 7/2002 | Petrich et al. |
| 6,420,181 B1 | 7/2002 | Novak |
| 6,450,810 B1 | 9/2002 | Fischer et al. |
| 6,451,607 B1 | 9/2002 | Lawrence et al. |
| 6,494,856 B1 | 12/2002 | Zygmont |
| 6,497,688 B2 | 12/2002 | Lasko |
| 6,503,013 B2 | 1/2003 | Strauss |
| 6,541,194 B2 | 4/2003 | DiCesare |
| 6,625,839 B2 | 9/2003 | Fischer et al. |
| 6,634,051 B1 | 10/2003 | Dragan et al. |
| 6,638,067 B2 | 10/2003 | Fischer et al. |
| 6,676,609 B1 | 1/2004 | Rutenberg et al. |
| D489,535 S | 5/2004 | Dragan |
| 6,732,743 B1 | 5/2004 | Bouix et al. |
| 6,881,554 B2 | 4/2005 | DiCesare et al. |
| 6,887,681 B2 | 5/2005 | DiCesare et al. |
| 6,929,475 B2 | 8/2005 | Dragan |
| 7,022,289 B1 | 4/2006 | Schlein et al. |
| 7,198,623 B2 | 4/2007 | Fischer et al. |
| 7,261,483 B2 | 8/2007 | Gueret |
| 7,582,067 B2 | 9/2009 | Van Acker |
| 7,645,608 B2 | 1/2010 | Greene |
| 8,114,027 B2 | 2/2012 | Triva |
| 8,133,193 B2 | 3/2012 | Van Acker |
| 8,317,728 B2 | 11/2012 | Triva |
| 8,631,715 B2 | 1/2014 | Triva |
| 8,772,034 B2 | 7/2014 | Rasch-Menges et al. |
| 9,170,177 B2 | 10/2015 | Triva |
| 9,428,788 B2 | 8/2016 | Triva |
| 9,504,452 B2 | 11/2016 | Triva |
| 10,092,275 B2 | 10/2018 | Triva |
| 2001/0008614 A1 | 7/2001 | Aronowitz et al. |
| 2002/0001539 A1 | 1/2002 | DiCesare et al. |
| 2002/0197738 A1 | 12/2002 | Matsumoto et al. |
| 2003/0073932 A1 | 4/2003 | Varey |
| 2003/0108846 A1 | 6/2003 | Hoertsch |
| 2003/0120180 A1 | 6/2003 | Kaylor et al. |
| 2004/0014063 A1 | 1/2004 | Batteux et al. |
| 2004/0078219 A1 | 4/2004 | Kaylor et al. |
| 2004/0158188 A1 | 8/2004 | Kauffmann et al. |
| 2004/0197730 A1 | 10/2004 | Rowe et al. |
| 2005/0181517 A1 | 8/2005 | Chandler et al. |
| 2005/0223511 A1 | 10/2005 | Mangold et al. |
| 2005/0223512 A1 | 10/2005 | Mangold et al. |
| 2005/0267395 A1 | 12/2005 | Mangold et al. |
| 2005/0288616 A1 | 12/2005 | Bozenbury et al. |
| 2006/0115805 A1 | 6/2006 | Hansen et al. |
| 2006/0142668 A1 | 6/2006 | Triva |
| 2006/0211978 A1 | 9/2006 | Do |
| 2006/0258250 A1 | 11/2006 | Mangold et al. |
| 2007/0105186 A1 | 5/2007 | Gibson et al. |
| 2007/0208274 A1 | 9/2007 | Ostrowski et al. |
| 2007/0255175 A1 | 11/2007 | Sangha |
| 2007/0275101 A1 | 11/2007 | Lu et al. |
| 2009/0024060 A1 | 1/2009 | Darrigrand et al. |
| 2009/0030054 A1 | 1/2009 | Warmington et al. |
| 2009/0030341 A1 | 1/2009 | Kshirsagar et al. |
| 2009/0186057 A1 | 7/2009 | Farmer et al. |
| 2009/0325861 A1 | 12/2009 | Goodheart |
| 2010/0112725 A1 | 5/2010 | Babu et al. |
| 2010/0249649 A1 | 9/2010 | Larkin |
| 2011/0281754 A1 | 11/2011 | Fischer et al. |
| 2011/0306078 A1 | 12/2011 | Triva |
| 2012/0150088 A1 | 6/2012 | Triva |
| 2012/0171712 A1 | 7/2012 | Triva |
| 2012/0271196 A1 | 10/2012 | Triva |
| 2013/0072817 A1 | 3/2013 | Triva |
| 2013/0338535 A1 | 12/2013 | Triva |
| 2014/0083213 A1 | 3/2014 | Triva |
| 2014/0106445 A1 | 4/2014 | Triva |
| 2017/0027549 A1 | 2/2017 | Triva |
| 2019/0008489 A1 | 1/2019 | Triva |
| 2019/0307433 A1 | 10/2019 | Triva |

FOREIGN PATENT DOCUMENTS

| | | |
|---|---|---|
| CN | 2460050 | 11/2001 |
| CN | 2479505 | 2/2002 |
| CN | 2554995 | 6/2003 |
| CN | 201131761 | 10/2008 |

(56) References Cited

FOREIGN PATENT DOCUMENTS

| | | |
|---|---|---|
| CN | 101765551 | 6/2010 |
| CN | 201993241 | 9/2011 |
| DE | 2552172 A1 | 6/1977 |
| DE | 2552172 B2 | 9/1977 |
| DE | 2755341 | 6/1979 |
| DE | 68904499 | 8/1993 |
| DE | 29809833 | 6/1998 |
| DE | 69507667 | 6/1999 |
| DE | 19937571 | 2/2000 |
| DE | 10246379 | 4/2004 |
| EP | 0223745 | 5/1987 |
| EP | 0354823 | 2/1990 |
| EP | 0244156 | 4/1990 |
| EP | 0527909 | 3/1993 |
| EP | 0643131 | 3/1995 |
| EP | 0568556 | 7/1995 |
| EP | 0693263 | 1/1996 |
| EP | 0707836 | 4/1996 |
| EP | 1147746 | 10/2001 |
| EP | 1358818 | 11/2003 |
| EP | 1382730 | 1/2004 |
| EP | 1608268 | 11/2007 |
| EP | 2395337 | 12/2011 |
| FR | 2729545 | 7/1996 |
| GB | 406850 | 3/1934 |
| JP | 62-231081 | 10/1987 |
| JP | 05-027671 | 4/1993 |
| JP | 10-024065 | 1/1998 |
| JP | 10-192050 | 7/1998 |
| JP | 11-514849 | 12/1999 |
| JP | 2000-152817 | 6/2000 |
| JP | 2000232982 | 8/2000 |
| JP | 2000342591 | 12/2000 |
| JP | 2001-346626 | 12/2001 |
| JP | 2002067201 | 3/2002 |
| JP | 2004000587 | 1/2004 |
| JP | 4579902 | 11/2010 |
| WO | WO 85/05296 | 12/1985 |
| WO | WO 198910724 | 11/1989 |
| WO | WO 199212863 | 8/1992 |
| WO | WO 97/03209 | 1/1997 |
| WO | WO 200009984 | 2/2000 |
| WO | WO 200054024 | 9/2000 |
| WO | WO 2004086979 | 10/2004 |
| WO | WO 2005013759 | 2/2005 |
| WO | WO 2005110316 | 11/2005 |
| WO | WO 2007075412 | 7/2007 |
| WO | WO 2008131033 | 10/2008 |
| WO | WO 2009018607 | 2/2009 |
| WO | WO 2009134509 | 11/2009 |
| WO | WO 2009136892 | 11/2009 |
| WO | WO 2009140356 | 11/2009 |
| WO | WO 2009158403 | 12/2009 |
| WO | WO 2011154849 | 12/2011 |

OTHER PUBLICATIONS

[No Author Listed], "ASM's Interim Algorithm for Guidance in Testing of Patients with Respiratory Illness for Influenza A (including Novel H1N1)", American Society for Microbiology, Sep. 2009, 1 page.
[No Author Listed], "HydraFlock: The Superior Flocked Swab," Mar. 2017, [retrieved on Mar. 4, 2017], Retrieved from: URL <http://blog.puritanmedproducts.com/whyhydaflockissuperiorflockedswab>, 3 pages.
"Safety Data Sheet in Accordance with Regulation 453/2010", Jun. 6, 2011, 6 pages.
2008 Fredrick D. Simon Award, Presented to: Gilberto Dalmaso, PhD, "Qualification of High-Recovery, Flocked Swabs as Compared to Traditional Rayon Swabs for Microbiological Environmental Monitoring of Surfaces," Published May/Jun. 2008, 1 page.
$4^{th}$ Opinion of the Defendants, German Application No. DE 20 2004 021 930, Nov. 27, 2015, 7 pages.
Appeal reasoning of Jul. 1, 2011, complaint T0954/11-3202 in EP Patent No. 1,608,268, 12 pages (machine translation).
Applied Biosystems, Benchmarking of applicators, Dec. 19, 2006, 26 pages.
Bersev et al. "Elektrostatische Beflockung", Leipzig, 1993, 127-129, 3 pages (machine translation).
Bersev et al., "Tables 5-8," Elektrostatische Beflockung, Leipzig, 1993, 3 pages (machine translation).
BG-Information, BGI 764, p. 7, Oct. 2000, including translation from http://babelfish.yahoo.com/translate_txt, and further as a concise statement of relevance Applicant submits that the reference was cited in the European Notice of Opposition in EP 04 724 556.8.
Blog.puritanmedproducts.com [online], "Which is the Best Type of Swab to Use when Diagnosing the Flu" Nov. 20, 2015, [retrieved on Aug. 27, 2020], retrieved from: URL <https://blog.puritanmedproducts.com/which-is-the-best-type-of-swab-to-use-when-dia>, 3 pages.
Boyle et al., "Optimization of an in vitro assay to detect *Streptococcus equi* subs. equi," Veterinary Microbiology, Oct. 12, 2012, 159(3-4):406-10.
Chernesky et al. Use of Flocked Swabs and a Universal Transport Medium to Enhance Molecular Detection of Chlamydia trachomastis and Neisseria gonorrhoeae; JCM, vol. 44, No. 3, Mar. 2006, 3 pages.
Chinese First Office Action, Chinese Application No. 201280004723.8, dated Sep. 29, 2014, 14 pages.
Chinese Second Office Action, Chinese Application No. 20120004723.8, dated May 18, 2015, 11 pages.
Clinician's Handbook of Preventive Services, US Dept. of Health and Human Services; Public Health Service, Office of Disease Prevention and Health Promotion, p. 196; 1994.
Communication pursuant to Article 94(3) EPC, European Application No. 12703153.2, Jan. 29, 2015, 7 pages.
Copan Flock Technologies SrL, Cytology—Cervical Collection, Copyright 2012, 2 pages.
*Copan Italia S.P.A. et al.* v. *Puritan Medical Products Company LLC et al.*, "Claim Construction Order", Case [1:18-cv-00218-JDL], U.S. Pat. No. 8,114,027, dated Nov. 4, 2019, 31 pages.
Corina et al., "Post-coital vaginal sampling with nylon flocked swabs improves DNA typing," Forensic Science International: Genetics, Feb. 1, 2010, 4(2):115-21.
Cotton—Facts and General Information from Swicofil, http:/lwww.swicofil.com/products/001cotton.html, Jan. 3, 2011, 9 pages.
Cotton—Wikipedia, the free encyclopedia, http://en.\wikipedia.org/wiki/Cotton, Jan. 3, 2011, 12 pages.
Daley et al., "Comparison of Flocked and Rayon Swabs for Collection of Respiratory Epithelial Cells from Uninfected Volunteers and Symptomatic Patients," Journal of Clinical Microbiology, Jun. 2006, 44(6):2265-2267.
Daniele Triva, "Method for Quantitative Transfer of Analytes" U.S. Appl. No. 12/840,087, filed Jul. 20, 2010, 25 pages.
Daniele Triva, "Swab for Collecting Biological Specimens" U.S. Appl. No. 10/543,873, filed Jul. 28, 2005, 10 pages.
Daniele Triva, "Swab for Collecting Biological Specimens" U.S. Appl. No. 12/903,921, filed Oct. 13, 2010, 8 pages.
Decision of Opposition Proceedings dated Jan. 25, 2011 in EP Application No. 0472556.8, foreign counterpart to present application, 13 pages.
Decision Under Appeal for European application No. 04724556.8-2113, dated Nov. 18, 2011, 30 pages.
Du et al. "Preparation of hydrophobic nylon fabric." Journal of Engineered Fibers and Fabrics 11.1, Mar. 11, 2016: 155892501601100106, 7 pages.
EP1608268—Minutes of the Oral Proceedings—Jun. 10, 2015, 4 pages.
EP1608268—Observations on behalf of Proprietor in reply to Opposition Brief dated Jan. 30, 2009, 15 pages.
EP1608268—Reply on behalf of patent proprietor re grounds of appeal—Nov. 18, 2011, 30 pages.
EP1608268—Reply on behalf of Proprietor and Remarks on Requests and Original Disclosure—Dec. 10, 2012, 54 pages.
EP1608268—Short Brief by Patent Proprietor—Oct. 28, 2014, 3 pages.
EP1608268_Observations filed by other party Jan. 30, 2009, 9 pages.

(56) References Cited

OTHER PUBLICATIONS

European Communication Pursuant to Article 94(3) EPC, European Application No. 12703153.2, dated Sep. 15, 2015, 4 pages.
Extract from Pschyrembel Klinisches Worterbuch, 255th edition, MB-B10, Published in 1986, 1533.
Extract from Saechtling, Kunststoff Taschenbuch, 26th edition, MB-B7, published in 1995, pp. 148-149, 2 pages.
FDA.gov [online], "FAQs on Testing for SARS-CoV-2" Jul. 2020, [retrieved on Aug. 26, 2020], retrieved from: URL <https://www.fda.gov/medical-devices/coronavirus-covid-19-and-medical-devices/faqs>, 103 pages.
File History for EP Application No. EP04724556, foreign counterpart to present application, up to Apr. 2011, 976 pages.
Flock Technology, Technical Academy of Esslingen; DE, Flock Diagram (with English Translation of Diagram) No. 13798/46,074, Apr. 17, 1991, 6 pages.
Gabler, Untersuchungen zum elektrostatisches Beflocken, RWTH Aachen, 1980, 1 page (machine translation).
Gabler; Studies on the Electrostatic Flocking (with English translation of table); RWTH Aachen Univ. 1980; 1 page.
Genetic Background, Basic Techniques for Bacterial Genetics, 3 pages.
German Application No. 20 2004 021 930.1, Order Pronounced in the Oral Proceedings of Jun. 9, 2015, 16 pages.
German Application No. 20 2004 021 932.8, Order Pronounced in the Oral Proceedings of Sep. 30, 2015, 32 pages.
German Federal Patent Court, Decision in the appeal case concerning DE Utility Model 20 2004 021 930.1, Sep. 13, 2016, 56 pages.
German Federal Patent Court, Minutes concerning DE Utility Model 20 2004 021 930, Sep. 13, 2016, 8 pages.
German Patent and Trademark Office, Decision in the Declaratory Proceedings, Mar. 11, 2016, 37 pages.
Ginocchio et al., "Current Best Practices for Respiratory Virus Testing," Journal of Clinical Microbiology, Sep. 2011, 49(9 Supp):S44-S48.
Grounds for Appeal dated Feb. 27, 2014, German Application No. Az. 20 2004 021 787.2, 13 pages (machine translation).
Grounds of Appeal, German Application No. DE 20 2004 021 930, Dec. 7, 2015, 30 pages.
Gynecological Specimens-Conventional Pap Test, Rutland Regional Health Services; prepared by Joe Walker Jr.; Jun. 10, 2011, 6 pages.
Hedin et al., New Technique to Take Samples from Environmental Surfaces Using Flocked Nylon Swabs; Journal of Hospital Infection 75, 2010, 4 pages.
Higher Regional Court of Düsseldorf Order to Take Evidence, *Copan Italia S.p.A.* v. *Puritan Medical Products Co., LLC et al.*, Apr. 7, 2016, 18 pages.
Hofmann et al., Adolescent Medicine, vol. 39, 1989, 2 pages (abstract only).
Int. Flock Symposium—Addendum to the General Assembly of the Assoc, of Flock Ind.; FLOCK vol. 16, Nr, 60/1990; Oct. 1990, 1 page (machine translation).
Int. Flock Symposium in Dresden excerpt Mar. 31-Apr. 1, 2003, 2 pages (machine translation).
It.usembassy.gov [online], "COVID 19 Emergency: Ambassador Eisenberg Praises Efforts by Italian Companies" Mar. 19, 2020, [retrieved on Aug. 25, 2020], retrieved from: URL <https://it.usembassy.gov/covid-19-emergency-ambassador-eisenberg-praises-efforts-b>, 1 page.
J.N. Bersev et al. „Elektrostatische Beflockung, Leipzig, 1993, 127-129, 3 pages (machine translation).
Japanese Office Action, Japanese Application No. 2013-547945, dated Oct. 2015, 7 pages.
Japanese Patent Office, Summarized English Translation of Notice of Reasons for Rejection, dated Jun. 21, 2016, 4 pages (28600-0006001 JP counterpart).
Leemans et al., "Evaluation of Methodology for the Isolation and Analysis of LCN-DNA before and after Dactyloscopic Enhancement of Fingerprints", Published in 2006, Elsevier, 583-585, 3 pages.

Magg, "Principles of Flocking," Adhesives Age, Sep. 1975, vol. 18, No. 9, 23-28, 6 pages.
Meissner Bolte, Munich, Rejoinder to Grounds of Appeal, DE Utility Model 20 2004 021 787.2, Oct. 4, 2016, 68 pages.
Michael L. Noel, MD: Papanicolaou Smear Adequacy: The Cervical Cytobrush and Ayre Spatula Compared with the Extended-Tip Spatula; Journal of the American Board of Family Practice, vol. 2, No. 3, Jul.-Sep. 1989, 5 pages.
Microrheologics, "New Technology for Sample Collection" 2006, 2 pages.
Millipore, "Flocked Swabs" 2007, 2 pages.
Moore et al. Dry Cotton or Flocked Respiratory Swabs as a Simple Collection Technique for the Molecular Detection of Respiratory Viruses Using Real-Time NASBA, JVM 153, 2008, 6 pages.
Mulder, Practical Guide for General Nursing Science Part 2 ; p. 195; May 31, 1999, 2 pages.
Munywoki et al., "Improved Detection of Respiratory Viruses in Pediatric Outpatients with Acute Respiratory Illness by Real-Time PCR Using Nasopharyngeal Flocked Swabs," Journal of Clinical Microbiology, Sep. 2011, 49(9):3365-3367, 3 pages.
Non-final office action issued in U.S. Appl. No. 16/132,081 dated Sep. 18, 2019, 24 pages.
Notice of Opposition to European Patent No. 1608268 dated Aug. 21, 2008, 15 pages.
Notice of Rejection for related Japanese patent application No. 2006-504927, dated Feb. 15, 2009, 4 pages.
Nugent et al., Evaluation of the Physical and Diagnostic Nature of Swabs, Department of Pathology, M44, 1 page.
Nytimes.com [online], "White House Enlist Military to Import Swabs for Coronavirus Tests" Mar. 20, 2020 [retrieved on Aug. 25, 2020], retrieved from: URL <https://www.nytimes.com/2020/03/20/US/politics/swabs-for-coronavirus-testing.html>, 5 pages.
Office action issued in U.S. Appl. No. 12/840,087 dated Oct. 9, 2012, 16 pages.
Office action issued in U.S. Appl. No. 13/043,175 dated Jun. 12, 2013, 10 pages.
Office Action issued in U.S. Appl. No. 13/361,584 dated Mar. 20, 2013, 16 pages.
Office action issued in U.S. Appl. No. 13/657,949 dated Jul. 1, 2013, 21 pages.
Office action issued in U.S. Appl. No. 13/657,949 dated Mar. 20, 2013, 16 pages.
Office Action dated Jan. 24, 2007 in related Canadian application No. 2,515,205, 11 pages.
Office Action dated Jan. 30, 2009 in related Australian application No. 2004226798, 2 pages.
Office Action dated Jul. 11, 2007 in related Australian application No. 541560, 2 pages.
Office Action, Federal Service for Intellectual Property, Russia, dated Nov. 2015, 5 pages.
Opinion of the Submissions by the Appellant, German Application No. DE 20 2004 021 930, Jun. 18 and 29, 2015, 11 pages.
Opinion on Contrary Justification—dated Jun. 30, 2014, German Application No. Az. 20 2004 021 787.2, 27 pages (machine translation).
Opposition filed 2011 against related Japanese application No. 2006-504297, including English translation, 12 pages.
PCT International Search Report and Written Opinion for international application IT MI20110004, dated Jul. 20, 2011, 7 pages.
PCT International Search Report and Written Opinion in International Application IT MI20101032, dated Feb. 24, 2011, 11 pages.
PCT International Search Report and Written Opinion in International Application No. IT MI201216032, dated May 6, 2013, 8 pages.
PCT International Search Report and Written Opinion of the International Searching Authority, PCT/IB2012/050018, dated Mar. 5, 2012, 11 pages.
PCT International Search Report in International Application WO 2004/086979, published Oct. 14, 2004, 2 pages.
Principles of Nonwovens, INDA, Association of the Nonwoven Fabrics Industry, Cotton's Unique Fiber Morphology, 1992, 11 pages.

(56) References Cited

OTHER PUBLICATIONS

Print of website http://www.flock.de/de/2_1_historie.php, believed to be Jul. 22, 2008, and including what is believed to be an English counterpart to the website printed from Print of website in English http://www.flock.de/pages/html/de/flock/sub/historie.html?lang=EN. Print of Website www.swicofil.com/flock.html, believed to be Aug. 16, 2002.
Puritan presentation of HydraFlock, The superior choice for specimen collection and release, 8 pages.
Register excerpt of UTM DE20 2004 021930 UI, Nov. 6, 2013, 3 pages (machine translation).
Relationship between flock length, fineness, thinness and process ability, Table 5 with English translation; p. 194,Leipzig 1993, 2 pages.
Response to the Appeal filed re German Utility Model DE202004021930U1 on Nov. 21, 2014, 12 pages.
Saegeman, "Comparison of Eswab with dry swab and Amies swab in maintaining viability of microorganisms and comparison of Eswab with dry swab for Gram stain quality," UZ Leuven, Laboratoriumgeneeskunde, May 19, 2010, 23 pages.
Samanta et al., "Hydrophobic Functionalization of Cellulosic Substrates Using Atmospheric Pressure Plasma" Cellulose Chemistry and Technology 50.7-8, Jul. 1, 2016, 10 pages.
Samu et al., "Effect of charge and hydrophobicity on adsorption of modified starches on polyester" Journal of colloid and interface science 220.2, Dec. 15, 1999, 2 pages.
Schenk, "Flock Trials in Laboratory With Alternating Current", International Flock Seminar, Sep. 8-10, 1980, 2 pages.
Specimen Submission Procedure for Gynecologic Cytology and HPV Testing, Dept. of Pathology, Crittenton Hospital Medical Pathology Department; Oct. 2014, 6 pages.
Streaking out individual colonies—2 days before lab, 2 pages.
Table 5 p. 194 of J.N. Bersev et al. „Elektrostatische Beflockung, Leipzig, 1993, (machine translation).
Textile Science and Technology: Absorbent Technology, Chatterjee & Gupta (ed)., 2002, 484 pages.
The City of Columbus Public Health, "Interim Recommendations for Collecting Clinical Specimens from Persons for Coronavirus Disease 2019 (covid-19)", Columbus Public Health, Jun. 24, 2020, 2 pages.
Thomasma, "A39 Optimization of Touch DNA Collection Techniques Using Alternative Swabbing Solutions", Proceedings American Academy of Forensic Sciences, XP055163017, Apr. 2010, pp. 40-41, 4 pages.
Thomasma, "The Influence of Swabbing Solutions on DNA Recovery from Touch Samples", Journal of Forensic Sciences, vol. 58, No. 2, Mar. 2013, 6 pages.
Traditional Method of Pure Culture Isolation of Bacteria, Single Colony Isolation of Bacteria; https://www.sonoma/edu/users/c/cannon/240singlecolonyisolation.html retrieved on Oct. 31, 2014, 2 pages.
Translation of Chilean office action issued in Chilean Application No. 3435-12, in reference to documents dated Apr. 16, 2013, 20 pages.
U.S. Patent Office's File for U.S. Appl. No. 10/543,873, filed Jul. 28, 2005, entitled "Biological Specimens", inventor Daniele Triva, 758 pages.
U.S. Patent Office's File for U.S. Appl. No. 12/840,087, filed Jul. 20, 2010, entitled "Method for Quantitative Transfer of Analytes", inventor Daniele Triva, 179 pages.
U.S. Patent Office's File for U.S. Appl. No. 12/903,921, filed Oct. 13, 2010, entitled "Swab for Collecting Biological Specimens", inventor Daniele Triva, 189 pages.
U.S. Patent Office's File for U.S. Appl. No. 13/043,175, filed Mar. 8, 2011, entitled "A Process for Realising a Device for Collecting and Transferring Samples for Molecular Biology", inventor Daniele Triva, 105 pages.
U.S. Patent Office's File for U.S. Appl. No. 13/531,800, filed Jun. 25, 2012, entitled "Swab for Collecting Biological Specimens", inventor Daniele Triva, 2453 pages.
U.S. Patent Office's File for U.S. Appl. No. 13/657,949, filed Oct. 23, 212, entitled "Swab for Collecting Biological Specimens", inventor Daniele Triva, 7,886 pages.
U.S. Patent Office's File for U.S. Appl. No. 13/661,376, filed Oct. 26, 2012, entitled "A Device and a Method for Collecting and Transferring Samples of Biological Material", inventor Daniele Triva, 79 pages.
U.S. Patent Office's File for U.S. Appl. No. 13/899,394, filed May 21, 2013, entitled "Swab for Collecting Biological Specimens", inventor Daniele Triva, 42 pages.
U.S. Patent Office's File2591 for U.S. Appl. No. 13/361,584, filed Jan. 30, 2012, entitled "Swab for Collecting Biological Specimens", inventor Daniele Triva, 174 pages.
Verhoeven et al. Better Detection of *Staphylococcus aureus* Nasal Carriage by Use of Nylon Flocked Swabs, JCM, vol. 48, No. 11, Nov. 2010, 3 pages.
What is Cotton Fibre/Properties of Cotton Fiber, http://articles.textileclass.com/cotton-fibre-what-is-cotton-fibre-cotton-f. May 11, 2011, 1 page.
Wikipedia, "Cotton Swab" http//en.wikipedia.org/wiki/Cotton swab, Jun. 22, 2011, 3 pages.
Wikipedia, "Swab" http://en.wikipedia.org/wiki/Swab, Jun. 22, 2011, 1 page.
Wurmb-Schwardk, "Fast and Simply DNA Extraction from Saliva and Sperm Cells Obtained from the Skin or Isolated from Swabs", Elsevier—Legal Medicine, Mar. 2006, 6 pages.

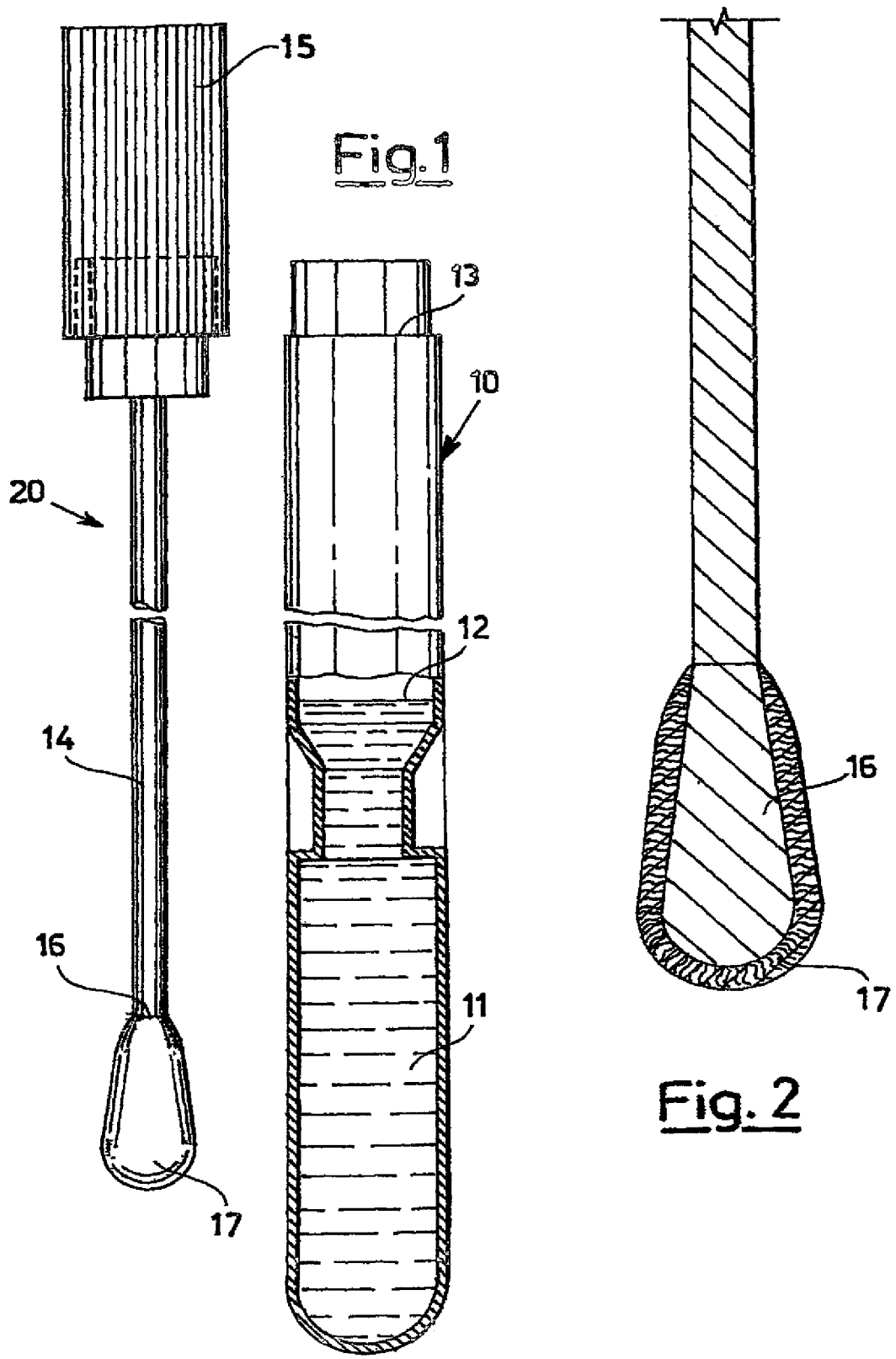

SWAB FOR COLLECTING BIOLOGICAL SPECIMENS

CROSS REFERENCE TO RELATED APPLICATIONS

This Application is a continuation of and claims the benefit under 35 U.S.C. § 120 of U.S. patent application Ser. No. 13/657,949, entitled "Swab for Collecting Biological Specimens," filed Oct. 23, 2012, which is a continuation of U.S. patent application Ser. No. 12/903,921 entitled "Swab for Collecting Biological Specimens," filed Oct. 13, 2010, now issued as U.S. Pat. No. 8,317,728 on Nov. 27, 2012, which is a continuation of U.S. Pat. No. 8,114,027, entitled "Swab for Collecting Biological Specimens," filed Jul. 28, 2005, that claims priority under 35 U.S.C. § 365 of PCT/EP2004/003392 filed Mar. 31, 2004, and that claims priority under 35 U.S.C. § 119 of Italian Application No. MI2003A000643 filed Apr. 1, 2003. Applicant incorporates by reference herein the disclosures of these applications and patent.

FIELD OF THE INVENTION

The present invention relates to a swab for collecting biological specimens.

BACKGROUND OF THE INVENTION

In the field of clinical and diagnostic analyses, swabs for collecting biological specimens of organic material are known, consisting essentially of a cylindrical rod around one end of which, known as the tip, is wrapped a wad of fibre such as rayon or a natural fibre such as cotton, with hydrophilic properties to allow rapid absorption of the quantity of specimen to be collected and tested. Stable adherence of the fibre wrapped around the tip of the rod is generally achieved by gluing.

Usually, especially if the specimen is to be examined by culturing the microorganisms gathered with the collection, a swab is immersed in a test-tube containing culture medium immediately after collection for appropriate conservation of the specimen during storage and/or transport thereof to the analytical laboratory.

An example of this type of device is given in patent EP0643131 by the same Applicant and refers to a swab for collecting and in vitro transporting specimens, of the type comprising a test-tube with culture medium in gel form and a rod carrying at one end a stopper for sealing the test-tube and at the opposite end means for collecting said specimen, for example a wad of fibre wrapped around the tip of the rod, to be dipped into the culture medium.

The tip of the cylindrical rod, generally manufactured from essentially rigid material such as plastic, for example by extrusion, commonly presents a truncating cut which would make it difficult to insert the swab rod into the cavities (oral, nasal, ocular or rectal, urethral, vaginal etc.) of the patient from whom the specimen is taken, if the tip is not adequately protected. Therefore, the wad of hydrophilic fibre wrapped around said truncated end must not only contain sufficient material to allow absorption of the specimen in the desired quantity, in general 100 microlitres, but must also have a sufficiently thick and rounded shape to sheathe the edge of the truncated end so that it cannot cause damage or irritation to the patient during specimen collection. For this reason the fibre wad is wrapped around the tip of the rod in a rounded shape, typically developing into an ogive or similar shape so that it gradually becomes thicker towards the end of the rod thus reaching maximum thickness and therefore maximum protective effect, precisely around the truncated end. A wad of such a shape, while protecting the patient from any risk of contact with said truncated end of the rod, results in a number of drawbacks. The main one is that the thickness of the wad, because of the hydrophilic nature of the fibre, leads to penetration of collected liquid specimen into the mass of said wad. As, for practical reasons, the sample is released from the swab at the moment of analysis by simply gripping the rod of the swab and delicately sliding its tip and hence the fibre impregnated with liquid, along for example a petri dish with culture medium, in practice by spreading the specimen onto this latter (swabbing), even if this operation is repeated and is careful, it does not enable the entire volume e.g. the 100 ml of absorbed specimen to be released, because that part of it which has penetrated into the interior of the wad in the direction of its tip cannot be pressed out towards the surface and hence released by the swab during this operation Due to this defect, on average only about 40% of the liquid specimen collected can in practice be recovered for analysis. Such loss of specimen translates inevitably into reduced sensitivity of analysis and increased false negatives. In this respect, referring to the aforementioned average specimen loss after swabbing the swab, by testing only the 40 microlitres released for swabbing out of the 100 microlitres of specimen initially collected, it becomes difficult to establish whether a negative test effectively refers to the absence of the microorganism sought or rather to its non- or insufficient transfer from swab to test plate.

A further problem derived from the bulky fibre wad of a swab of the known art is particularly evident for example in the case of urethral or ocular use of said swab. In these and other particular applications it would actually be even more desirable to be able to minimize swab thickness and hence patient discomfort during collection.

SUMMARY OF THE INVENTION

As a solution to these problems, and also to achieve other advantages which will be apparent from the description, the present invention proposes a swab for collecting biological specimens of the type consisting of a rod terminating with a tip covered in fibre with hydrophilic properties to allow absorption of said specimens, characterised In that said fibre covers said tip In the form of a layer applied by means of flocking.

With the aim of better understanding the characteristics and advantages of the invention, a non-limiting example of a practical embodiment thereof is described hereinafter, with reference to the figures of the accompanying drawings. Said example refers to the case of a swab suitable for both the collection and storage of a biological specimen, and therefore also includes a test-tube containing a culture medium suitable for the collected microorganisms into which the swab is to be immersed after collection, such as for example the type described in the aforementioned patent EP0643131 by the same Applicant.

BRIEF DESCRIPTION OF THE FIGURES

FIG. 1 shows an exploded view of the two components of a device in accordance with the example, that is the swab and test-tube, whereby the test-tube is partially sectioned longitudinally.

FIG. 2 shows an enlarged detail of the swab of FIG. 1 in section.

DETAILED DESCRIPTION OF THE INVENTION

With reference to said figures, a device of the invention in accordance with the illustrated example comprises an essentially cylindrical test-tube 10 containing a culture medium in gel form 11, presenting a free surface level 12 inside the test-tube.

The upper open end of the test-tube presents a collar 13 for receiving a closure means.

The device is completed by a swab 20 consisting of a rod 14 carrying at one end a stopper 15 which has to act as the closure means of the test-tube and is hence shaped so that it can engage, for example by snap-engaging, with the collar 13 of the test-tube.

At the opposite end, the rod 14 terminates with a tip 16 carrying a suitable means, for example a layer of fibre 17, for collecting the specimen to be analysed. In the illustrated example, said tip 16 of the rod is shaped in a rounded geometry, similar to an ogive, and said fibre 17 being disposed as a layer of uniform thickness.

In general terms, in accordance with the fundamental characteristic of the invention, said fibre with hydrophilic properties is deposited by means of flocking. The flocking technique is preferably of the type conducted in an electrostatic field which deposits the fibres in an ordered manner, perpendicular to the surface of the tip of the swab rod, which has been previously coated with adhesive for example by immersion or spraying.

The fibre which is to form the flocked layer is subjected to an electrostatic field, and is hence deposited in an oriented manner and anchored to the surface of the tip, being retained by the adhesive.

The adhesive is preferably water-based: once dried it enables the fibre to be anchored in a stable manner to the swab and to resist abrasion.

The flocked swab is then dried by exposing it to a source of heat or radio-frequency.

The tip of the swab stem is covered with a layer of fiber, preferably of uniform thickness, and from 0.6 to 3 mm thick. The fiber count, i.e. the weight in grams per 10,000 linear meters of a single fiber, is preferably between, 1.7 and 3.3 Dtex. In particular, a fiber of 0.6 mm length and 1.7 Dtex can be applied by flocking to obtain a fine nap, and a fiber up to 3 mm in length and 3.3 Dtex can be applied to obtain a long nap, obtaining, for values intermediate between the aforedefined, corresponding intermediate characteristics of thickness and fineness of the flocked layer.

Within the wide choice of such values, the expedient to be respected according to the objects of the invention is to maintain an ordered arrangement of the fibres, substantially parallel to each other and normal to the surface of the rod, avoiding any overlapping of fibres which can occur if the nap is too long. Indeed, in this manner the capillary represented by each fibre, by virtue of which it can carry out its task of absorbing and releasing essentially the same quantity of specimen, remains unimpaired and functional.

The amount of fibre to be deposited for forming the flocked layer in accordance with the invention is determined on the basis of the type of fibre and the pre-chosen layer characteristics of thickness and fineness, in such a manner as to enable 100 microlitres of specimen to be absorbed.

In accordance with the objects of the invention, the fibre is chosen from a wide range of materials provided they are hydrophilic by capillarity, such as for example, synthetic or artificial materials e.g. rayon, polyester, polyamide, carbon fibre or alginate, natural materials e.g. cotton and silk, or mixtures thereof.

EXAMPLES

Some preparative examples are now given of a swab according to the invention. Such examples are not intended in any way to limit the scope of the invention.

Example 1

A swab is prepared using a plastic rod, suitable for human clinical collection, of diameter 2.5 mm which decreases to 1 mm over a length of about 6 cm.

The tip of the part with the smallest diameter is dipped in or sprayed with an adhesive, then the rod is placed vertically in a flocking apparatus in electrostatic field to deposit a polyamide flock.

The polyamide flock of 0.7 mm length and 1.7 Dtex allows 0.5 µl per mm$^2$ to be absorbed, therefore by flocking the 10 mm long tip of said rod the absorbing capacity obtained is 40 µl.

Example 2

Proceeding as per example 1, a rod with a spatulate end is used, suited for example to collecting organic specimens from the oral cavity of a patient. Polyester fibre of 1 mm length and 1.7 Dtex count are used for the flocking.

Example 3

Proceeding as per examples 1 and 2, polyester fibre of 2 mm length and 2.5 Dtex count is used.

Continuing in general terms, it is calculated that a swab of the invention is capable of releasing about 90% of the absorbed specimen by swabbing, in this manner considerably increasing the sensitivity of the analysis compared with swabs of the known art, in particular by almost completely eliminating the risk of false negatives resulting from the incomplete release of the collected specimen from swab to test plate.

In addition, the fact of being able to form, according to the invention, a fibre layer of any thickness, even very small, around the tip of the rod rather than a mass to cover it, as in the known art, means that the required rounded shape of the swab, i.e. free of edges, no longer has to depend on the mass of fibre itself but on the tip of the rod, which can therefore be preferably shaped into a round form, as indeed occurs in the aforedescribed example and shown in the accompanying drawings. Particularly in specific cases where swabs of the greatest possible thinness are required, for example urethral or ocular, this represents a further definite advantage over known swabs. Indeed a swab can be provided with a rounded tip by virtue of its shaping, around which a thin layer of fibre is deposited by flocking to allow on the one hand collection of a sufficient quantity of specimen for analysis, and on the other to minimize the total bulk of the part of the swab which is to penetrate the urethra, in consequence so reducing the discomfort of the patient undergoing the collection procedure.

The shape given to the tip of the swab nevertheless varies greatly according to the type of collection it is intended for, and can even be truncated or have edges when the type of collection (for example oral) allows it.

According to the invention, the type of adhesive, type of fibre and fibre characteristics, such as length and count, are in any case chosen from a wide range of options in order to obtain an ideal specific marker for identifying the microbiological specimen, whether by a direct diagnostic technique, by immuno-test, or by molecular biology techniques such as PCR, or with other known culturing, enrichment or selection techniques.

The specimen to be collected with a swab of the invention generally consists of bacteria or viruses or DNA or RNA or a mixture thereof.

The invention claimed is:

1. A biological specimen collection swab, comprising:
    a rod terminating in a tip, the tip being shaped with a rounded geometry; and
    a layer of fibers disposed on a surface of said tip by flocking with a flocking technique in which the fibers were deposited in an ordered manner on the surface of the tip of the rod, the layer of fibers having a fiber length of 0.6 to 3 mm and being configured to have capillarity hydrophilic properties and configured to and having an amount of fiber capable of absorbing by capillarity a quantity of 40 µl of liquid biological specimen in said layer of fibers on the tip of the rod, the liquid absorption capacity of said layer of fibers being at least 40 µl, and
    wherein said swab is configured to collect said biological specimen from a human for analysis.

2. The swab as claimed in claim 1 wherein said rod is a plastic rod and said rod tip is rigid.

3. The swab as claimed in claim 1 wherein capillaries are defined in said layer of fibers to confer hydrophilic properties by capillarity to the layer of fibers.

4. The swab as claimed in claim 1 wherein the swab is a clinical swab configured for human clinical collection of said biological specimens.

5. The swab as claimed in claim 1 wherein the swab is a clinical swab which is sterilized and configured for human clinical collection of said biological specimens from a human body cavity.

6. The swab as claimed in claim 1 wherein the swab is sterilized and configured and destined for insertion into, and sample collection from, a body cavity of a patient, the body cavity comprising one or more of an oral, nasal, ocular ureteral, rectal or vaginal cavity of a human.

7. The swab as claimed in claim 1 wherein the swab is a nasopharyngeal swab which is configured to be inserted into a nasal cavity of a patient.

8. The swab as claimed in claim 1 wherein the fibers of the layer of fibers have a fiber count of 1.7 to 3.3 Dtex.

9. A biological specimen collection swab, comprising:
    a rod terminating in a tip, the tip being shaped with a rounded geometry; and
    a layer of fibers disposed on a surface of said tip by electrostatic flocking, the layer of fibers having a fiber length of 0.6 to 3 mm and being configured to have capillarity hydrophilic properties and configured to and having an amount of fiber capable of absorbing by capillarity a quantity of 40 µl of liquid biological specimen in said layer of fibers on the tip of the rod, the liquid absorption capacity of said layer of fibers being at least 40 µl, and
    wherein said swab is configured to collect said biological specimen from a human for analysis.

10. The swab as claimed in claim 9 wherein said rod is a plastic rod and said rod tip is rigid.

11. The swab as claimed in claim 9 wherein capillaries are defined in said layer of fibers to confer hydrophilic properties by capillarity to the layer of fibers.

12. The swab as claimed in claim 9 wherein the swab is a clinical swab configured for human clinical collection of said biological specimens.

13. The swab as claimed in claim 9 wherein the swab is a clinical swab which is sterilized and configured for human clinical collection of said biological specimens from a human body cavity.

14. The swab as claimed in claim 9 wherein the swab is sterilized and configured and destined for insertion into, and sample collection from, a body cavity of a patient, the body cavity comprising one or more of an oral, nasal, ocular ureteral, rectal or vaginal cavity of a human.

15. The swab as claimed in claim 9 wherein the swab is a nasopharyngeal swab which is configured to be inserted into a nasal cavity of a patient.

16. The swab as claimed in claim 9 wherein the layer of fibers is configured to and has an amount of fiber capable of absorbing by capillarity a quantity of 100 µl of liquid biological specimen in said layer of fibers on the tip of the rod, the liquid absorption capacity of said layer of fibers being at least 100 µl.

17. The swab as claimed in claim 9 wherein the fibers of the layer of fibers have a fiber count of 1.7 to 3.3 Dtex.

18. A biological specimen collection swab, comprising:
    a rod terminating in a tip, the tip being shaped with a rounded geometry; and
    a layer of fibers disposed on a surface of said tip by flocking, the fibers having a length of 0.6 to 3 mm and the layer of fibers being configured to have capillarity hydrophilic properties and configured to and having an amount of fiber capable of absorbing by capillarity a quantity of 40 µl of liquid biological specimen in said layer of fibers on the tip of the rod, the liquid absorption capacity of said layer of fibers being at least 40 µl, and
    wherein said swab is a configured to collect said biological specimen from a human for analysis.

19. The swab as claimed in claim 18 wherein said rod is a plastic rod and said rod tip is rigid.

20. The swab as claimed in claim 18 wherein capillaries are defined in said layer of fibers to confer hydrophilic properties by capillarity to the layer of fibers.

21. The swab as claimed in claim 18 wherein the layer of fibers is configured to and has an amount of fiber capable of absorbing by capillarity a quantity of 100 µl of liquid biological specimen in said layer of fibers on the tip of the rod, the liquid absorption capacity of said layer of fibers being at least 100 µl.

22. The swab as claimed in claim 18 wherein the swab is a clinical swab configured for human clinical collection of said biological specimens.

23. The swab as claimed in claim 18 wherein the swab is a clinical swab which is sterilized and configured and destined for human clinical collection of said biological specimens from a human body cavity.

24. The swab as claimed in claim 18 wherein the swab is sterilized and configured and destined for insertion into, and sample collection from, a body cavity of a patient, the body cavity comprising one or more of an oral, nasal, ocular ureteral, rectal or vaginal cavity of a human.

25. The swab as claimed in claim 18 wherein the swab is a nasopharyngeal swab which is configured and destined to be inserted into a nasal cavity of a patient.

26. The swab as claimed in claim 18 wherein the swab is configured and destined to obtain a specific marker for identifying a microbiological specimen by a direct diagnostic technique.

27. The swab as claimed in claim 18 wherein the swab is configured and destined to obtain a specific marker for identifying a microbiological specimen by immunotest.

28. The swab as claimed in claim 18 wherein the swab is configured and destined to obtain a specific marker for identifying a microbiological specimen by molecular biology techniques.

29. The swab as claimed in claim 18 wherein the swab is configured and destined to obtain a specific marker for identifying a microbiological specimen by culturing techniques.

30. The swab as claimed in claim 18 wherein the fibers of the layer of fibers have a fiber count of 1.7 to 3.3 Dtex.

\* \* \* \* \*